US008697846B2

(12) United States Patent
Zimring

(10) Patent No.: US 8,697,846 B2
(45) Date of Patent: Apr. 15, 2014

(54) METHODS OF MAKING MONOCLONAL ANTIBODIES USING FUSION-PEPTIDE EPITOPE ADOPTIVE TRANSFER (F-PEAT) TECHNOLOGY

(75) Inventor: James C. Zimring, Decatur, GA (US)

(73) Assignee: Emory University, Atlanta, GA (US)

( * ) Notice: Subject to any disclaimer, the term of this patent is extended or adjusted under 35 U.S.C. 154(b) by 292 days.

(21) Appl. No.: 12/671,926

(22) PCT Filed: Aug. 15, 2008

(86) PCT No.: PCT/US2008/073276
§ 371 (c)(1), (2), (4) Date: Apr. 4, 2011

(87) PCT Pub. No.: WO2009/023816
PCT Pub. Date: Feb. 19, 2009

(65) Prior Publication Data

US 2011/0191866 A1 Aug. 4, 2011

Related U.S. Application Data

(60) Provisional application No. 60/964,770, filed on Aug. 15, 2007, provisional application No. 60/969,942, filed on Sep. 4, 2007.

(51) Int. Cl.

| | |
|---|---|
| ***C07K 16/00*** | (2006.01) |
| *C12N 5/0783* | (2010.01) |
| *C12N 5/16* | (2006.01) |
| *C07K 16/28* | (2006.01) |

(52) U.S. Cl.
CPC ............... *C07K 16/00* (2013.01); *C12N 5/0636* (2013.01); *C12N 5/16* (2013.01); *C07K 2319/00* (2013.01); *C07K 16/28* (2013.01)
USPC .................. 530/388.1; 530/387.9; 530/388.7; 424/144.1; 424/153.1; 424/93.71

(58) Field of Classification Search
None
See application file for complete search history.

(56) References Cited

U.S. PATENT DOCUMENTS 4,752,583 A * 6/1988 Jensen et al. ............... 530/388.7
5,573,916 A * 11/1996 Cheronis et al. ............... 435/7.1
5,969,109 A * 10/1999 Bona et al. ................. 530/387.3
6,228,987 B1 * 5/2001 Wang ............................ 530/324
6,376,459 B1 * 4/2002 Aruffo et al. .............. 424/134.1

FOREIGN PATENT DOCUMENTS

WO WO 9526365 A1 * 10/1995
WO WO 2004067553 A2 * 8/2004

OTHER PUBLICATIONS

Janeway et al., Immunobiology, $3^{rd}$ edition, 1997, Garland Publications, pp. 8:1-8:17.*

* cited by examiner

*Primary Examiner* — Michael Szperka
(74) *Attorney, Agent, or Firm* — Ballard Spahr LLP

(57) ABSTRACT

Disclosed are compositions and methods for related to monoclonal antibodies specific for single amino acid variation in an antigen.

10 Claims, 3 Drawing Sheets

Figure 1:
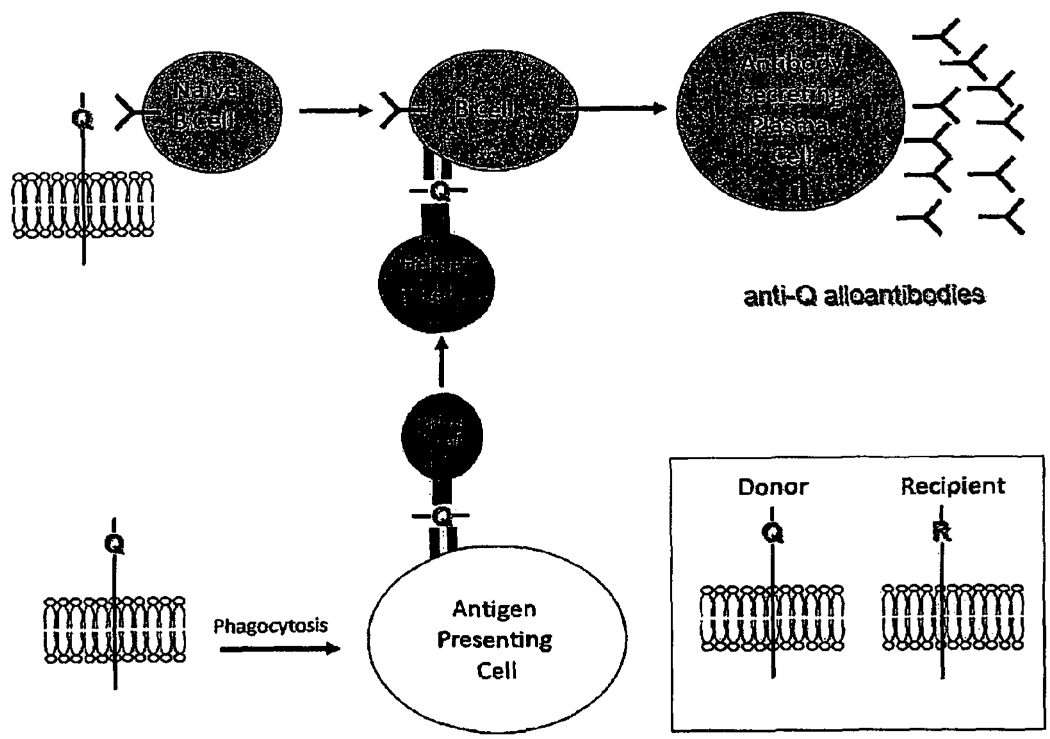

METHODS OF MAKING MONOCLONAL ANTIBODIES USING FUSION-PEPTIDE EPITOPE ADOPTIVE TRANSFER (F-PEAT) TECHNOLOGY

This application claims the benefit of U.S. Provisional Application No. 60/964,770, filed on Aug. 15, 2007, and U.S. Provisional Application No. 60/969,942, filed on Sep. 4, 2007 which are incorporated by reference herein in their entirety.

This application was made with government support under federal grants NIH HL084192 and HL 086312 awarded by the NIH. The Government has certain rights to this invention.

I. BACKGROUND

The generation of monoclonal antibodies against human proteins is a central component of molecular diagnostics and the development of protein based assays for human molecular medicine. Likewise, in some settings, monoclonal antibodies are highly efficacious therapeutic modalities. In both diagnostics and therapeutics, fine specificity of the antibody is often required. In some cases, such as blood typing and transfusion medicine, the antibodies are not useful unless they recognize the target epitope on the surface of an intact cell. For the vast majority of blood group antigens, the epitope of interest consists of a single amino acid polymorphism in an exofacial domain of the protein in question. In the United States alone, approximately 14 million units of red blood cells (RBCs) are transfused per year. Besides the well known ABO and RhD blood group antigens, several hundred additional antigens have been described, which vary widely throughout the genetically divergent human population. Thus, each transfusion recipient has the potential to make an antibody response against a wide array of foreign antigens. Once an antibody is made, it is often unsafe to transfuse additional RBCs that express the antigen; as such cells are lysed when recipient antibodies bind to them. The negative effects of this are not limited to a loss of the potential therapeutic effects of the transfused RBCs; indeed, the lysis of transfused RBCs can lead to renal failure, shock, disseminated intravascular coagulation, and in some cases death. It is for this reason that every transfusion recipient undergoes a screen for antibodies against RBC antigens prior to being transfused. In the event that an antibody is detected, its antigenic specificity is identified. The patient is then only transfused with RBCs that do not express antigens recognized by the recipient antibodies. Thus, potentially fatal hemolytic transfusion reactions are avoided.

In order to identify antigen-negative units of RBCs for patients who have developed an alloantibody, one must be able to phenotypically characterize antigens on the surface of donor RBCs. This is accomplished by incubating RBCs with antibodies specific for the antigen in question, under conditions that induce RBC agglutination, when the antibody recognizes the RBCs. Thus, to phenotypically characterize antigens on the surface of RBCs, one must have an extensive panel of antibody reagents, each of which recognizes a different relevant blood group antigen. Traditionally, such antibodies were acquired from antiserum of patients, who had previously become alloimmunized by a transfusion, and now served as donors to generate the antibody reagents. However, there are several problems in using human alloimmunized donors as the source for RBC typing antibodies, including: 1) Logistical problems of maintaining a consistent schedule of donation, 2) limited supply of serum given a donor safety concerns regarding frequency of donation, 3) questions of specificity as additional antibodies may also be present, 4) inconsistence of the reagents from donor to donor, and 5) changing of the nature of the antisera in a given donor as a function of time (changing titers, affinity maturation, etc.). It is for these reasons that monoclonal antibodies are highly desirable and superior as typing reagents. However, manufacture of human monoclonal antibodies can be very difficult; therefore, a number of human blood group antigens still do not have monoclonal antibodies that can recognize them (e.g. Duffy A, Duffy B, S antigen, etc.), and new approaches for detecting single amino acid polymorphisms as well as generating antibodies that are capable of detecting single amino acid polymorphisms are needed.

II. SUMMARY

Disclosed are methods and compositions related to monoclonal antibodies capable of distinguishing single amino acid determinants on an antigen.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows a diagram of antigen processing of a donor antigen consisting of an allelic amino acid variation. Here, B cells with a recombined immunoglobulin gene specific for the variant antigen binds to the antigen, endocytoses it, processes it and presents peptides on MHC class II. While antigen is being processed by specific B cells, other cells expressing the antigen are being phagocytosed by antigen presenting cells and are likewise being digested and presented on MHC class II molecules to CD4 T cells. CD4 T cells with T cell receptors specific for the antigen then bind to the antigen on the macrophage and after receiving co-stimulation, differentiate into helper T cells which provide help for the B cell, which becomes activated, undergoes isotype switching, affinity maturation; and can ultimately develop into an antibody secreting plasma cell.

Figure 2:
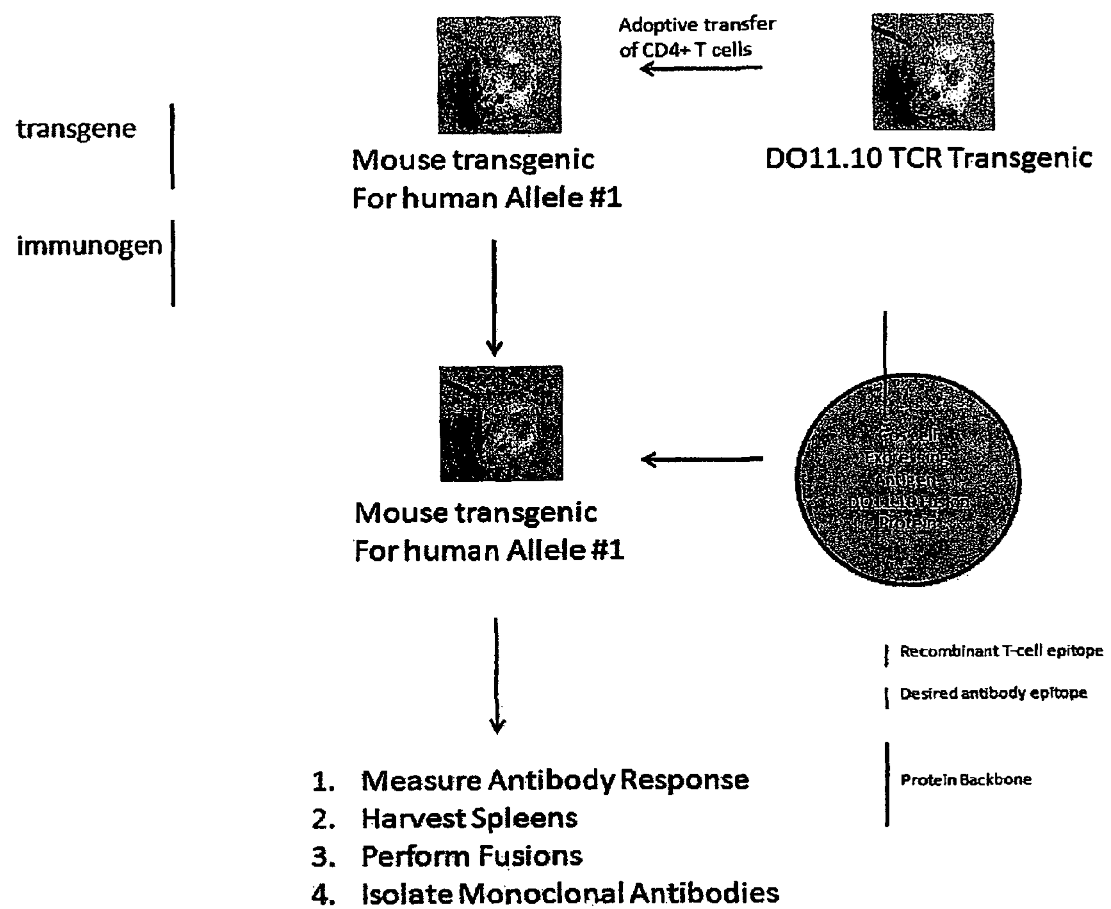

FIG. 2 shows a schematic diagram of the disclosed method for generating monoclonal antibodies to allelic variants.

Figure 3:
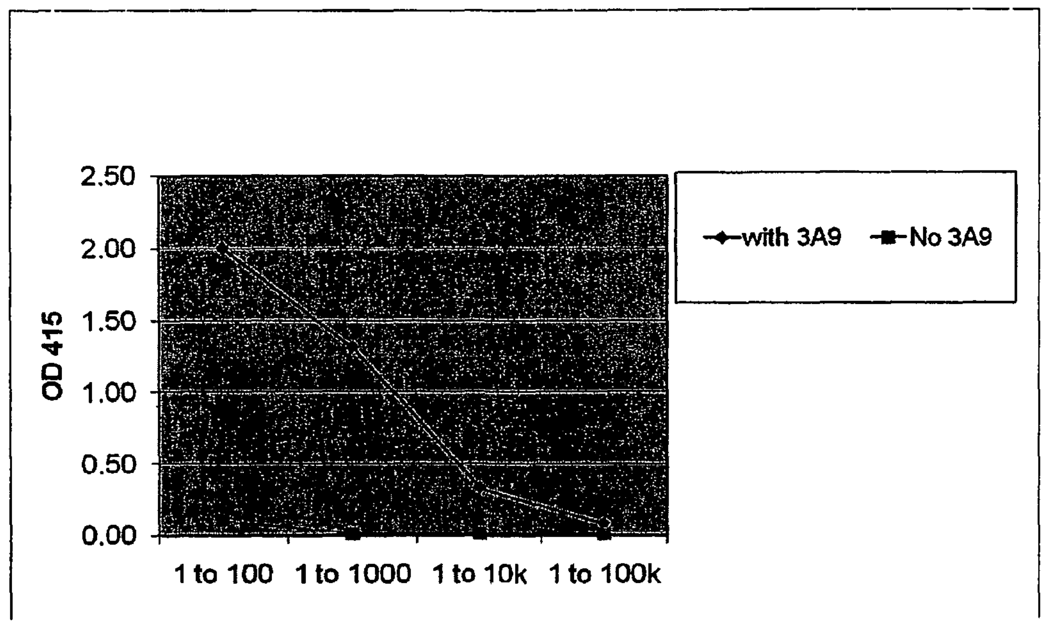

FIG. 3 shows the titration of an anti-HEL antibody made utilizing the disclosed methods 7 days post transfusion with mHEL RBC into mice that have received HEL specific CD4+ T Cells. As noted in the titration, enhancement is between 1:100 and 1:1000 (the control sample received an initial 1:100 dilution before the titration).

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms “a,” “an” and “the” include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

B. METHODS OF MAKING THE COMPOSITIONS

The generation of monoclonal antibodies against human proteins is a central component of molecular diagnostics and the development of protein based assays for human molecular medicine and monoclonal antibody therapeutics. In some cases, such as blood typing and transfusion medicine, the antibodies are not useful unless they recognize the target epitope on the surface of an intact cell. For the vast majority of blood group antigens, the epitope of interest consists of a single amino acid polymorphism in an exofacial domain of the protein in question. Although monoclonal antibodies can be made from humans who have been previously alloimmunized by transfusion, this is a difficult procedure with often disappointing results. However, despite the great utility of rodents in developing monoclonal antibodies in other settings, there are two main problems in the current context. First, homology between human and murine blood group antigens is poor. Thus, immunization of mice with human antigens results in multiple antibodies against various parts of the human molecule, but does not result in antibodies with the fine specificity that can distinguish the single amino acid polymorphisms in human blood group antigens. Second, a number of the blood group antigens are conformation dependant. Thus, purified protein antigens cannot be used, and intact cells expressing transfected antigen are required. In this case, the antibody response may be very weak and of low affinity for because infused cells are often not very immunogenic; and there are a variety of other foreign antigens on commonly transfected cells (e.g. COS or CHO cells which attract the majority of the antibody response, leaving only a small response to the molecule of interest). It is for these reasons that a number of human blood group antigens still do not have monoclonal antibodies that can recognize them (e.g. Duffy A, Duffy B, S antigen, etc.).

The issue of fine specificity is not limited to blood group antigens, but is relevant to any specificity that recognizes small differences between allelic variants of proteins, or requires that the molecule be folded in its correct conformation for the epitope to be present. For example, the issue of fine specificity is important for allelic variants between humans such as with hemoglobin, albumin, and cardiac enzymes.

Disclosed herein are methods and compositions that solve the above problems. The disclosed methods consist of making a transgenic mouse that expresses one allelic form of the protein in question. This animal is then immunized with the second allelic form. Since the animal is tolerized to the allelic form that it expresses as a transgene, its antibody response is immunologically focused on the differences found in the second allelic form. Because, in the case of blood group antigens, the variant allelic forms of the protein are conformationally dependent, the immunization with the second allelic form occurs by administering to the animal a cell that expresses the protein rather than the purified protein. To make the cells more immunogenic (or in some cases immunogenic at all), CD4 help is provided in the form of a T cell epitope known to fit well into the MHC class II pocket which is fused to a terminal end of the protein. The addition of this epitope is of particular importance, as the peptides containing the allelic variants in some antigens may not fit into the MHC II pocket due to a given subject's MHC restriction. In such instances, CD4+ helper T cells will not be able to be generated, even in the case of an adjuvant. Hence no antibodies would be made. This method insures adequate CD4 T cell help. To augment this process even further, the T cell epitope that is fused is chosen so that TCR transgenic mice exist, which encode a TCR that recognizes the epitope. This allows adoptive transfer for TCR transgenic cells prior to immunization, thus increasing the precursor frequency to high levels, and inducing a much more robust antibody response. Thus, disclosed herein are methods of making a monoclonal antibody comprising the steps of a) administering to a subject CD4 T cells specific for a first antigen; b) administering to a subject a cell comprising a chimeric antigen wherein the chimeric antigen comprises a first antigen linked to the terminal end of a second antigen; and c) harvesting the antibody specific to the second antigen. It is further understood that the subject can comprise a third antigen which is an allelic variant of the second antigen. Thus, also disclosed herein are methods of making a monoclonal antibody, wherein the subject expresses a third antigen and wherein the third antigen differs from the second antigen by a single amino acid variation. Also disclosed are antibodies made by the disclosed methods.

It is understood and herein contemplated that the CD4 T cells can be derived from any source for an antigen specific T cell such as a primary CD4 T cell, CD4 T cell line, or a transgenic animal. Thus disclosed herein are methods wherein the CD4 T cells are derived from a subject that is transgenic for the first antigen. Thus, disclosed herein are methods wherein the CD4 T cells are isolated from a second subject comprising T-cell receptor (TCR) transgene specific for the first antigen. It is further understood that TCR transgenic animals are well known in the art. Examples of TCR transgenic animals include but are not limited to 1H3.1 (I-Ea chain), 2B4 (Pigeon cytochrome C (PCC) 81-104), 3.L2 (human hemoglobin d allele 64-76), 3A9 (hen egg lysozyme (HEL) 46-61), 4B2A1 (MOPC315 IgG2 91-101), 5C.C7 (PCC 88-104), Influenza hemaglutinnin (HA) 111-119, A18 (complement protein C5 107-121), AND (PCC 88-104), B5 (IgG2ab 435-451), D011.10 (chicken ovalbumin 323-339), D10 (chicken conalbumin 134-146), Dep (human Reactive C Protein 89-101), MBP (murine myelin basic protein 121-150), OT-II (chicken ovalbumin protein 323-339), September (human Reactive C Protein 80-94), SM1 (salmonella flagellin 427-441), and TCR-HNT (influenza virus hemaglutinin 126-138). Thus, for example, disclosed herein are methods wherein the CD4 T cells are isolated from a second subject comprising T-cell receptor (TCR) transgene specific for the first antigen, wherein the first antigen is ovalbumin 232-330 and the second subject is a D011.10 mouse.

It is understood and herein contemplated that the second antigen can comprise any antigen against which raising of an antibody is desired. Thus for example, disclosed herein are methods wherein the second antigen is a blood antigen. Specifically disclosed herein are methods wherein the second antigen can be blood antigens such as ABO, MNS, P, Rh, Lutheran ($Lu^a$ and $Lu^b$), Kell and XK, Lewis ($Le^a$ and $Le^b$), Duffy ($Fy^a$ and $Fy^b$), Kidd ($Jk^a$ and $Jk^b$), Diego, XG, Scianna, Dombrock, Colton, Landsteiner-Wiener, Cartwright (Yt), Chido-Rogers, H substance (Hh), Kell precursor (Kx), Gerbich, Cromer, Knops, Indian, OK, Xg, Raph, John Milton Hagen (JMH), GIL, Cost, Er, Batty, Christiansen, Biles, Box, Torkildsen, Peters, Reid, Jensen, Livesey, Milne, Rasmussen, Oldeide, JFV, Katagiri, Jones, HJK, HOFM, SARAH, REIT, VEL, Lan Ata, Jra, Emm, AnWj, Sda PEL, ABTI, MAM, or any other antigen disclosed herein. Thus, for example, disclosed herein are methods wherein the blood antigen is selected from the listing of blood antigens consisting of Duffy A, Duffy B, Kell antigen $K_1$, Kell antigen $K_2$, S antigen, H substance; Yt(a), and Yt(b).

1. Blood Group Antigens

A blood type (also called a blood group) is a classification of blood based on the presence or absence of inherited antigenic substances on the surface of red blood cells (RBCs). These antigens may be proteins, carbohydrates, glycoproteins or glycolipids, depending on the blood group system, and some of these antigens are also present on the surface of other types of cells of various tissues. Several of these red blood cell surface antigens, that stem from one allele (or very closely linked genes), collectively form a blood group system. Examples of blood group antigens include but are not limited to ABO, MNS, P, Rh, Lutheran ($Lu^a$ and $Lu^b$), Kell and XK, Lewis ($Le^a$ and $Le^b$), Duffy ($Fy^a$ and $Fy^b$), Kidd ($Jk^a$ and $Jk^b$), Diego, XG, Scianna, Dombrock, Colton, Landsteiner-Wiener, Cartwright (Yt), Chido-Rogers, H substance (Hh), Kell precursor (Kx), Gerbich, Cromer, Knops, Indian, OK, Xg, Raph, John Milton Hagen (JMH), GIL, Cost, Er, Batty, Christiansen, Biles, Box, Torkildsen, Peters, Reid, Jensen, Livesey, Milne, Rasmussen, Oldeide, JFV, Katagiri, Jones, HJK, HOFM, SARAH, REIT, VEL, Lan Ata, Jra, Emm, AnWj, Sda PEL, ABTI, and MAM. It should be noted that the vast majority of the hundreds of described human blood group antigens are allelic variants of amino acids in proteins.

If an individual is exposed to a blood group antigen that is not recognized as self, the immune system produces antibodies that can specifically bind to that particular blood group antigen and an immunological memory against that antigen is formed. The individual will have become sensitized to that blood group antigen. These antibodies can bind to antigens on the surface of transfused red blood cells (or other tissue cells) often leading to destruction of the cells by recruitment of other components of the immune system.

The Duffy antigen gene (gp-Fy; CD234) is located on the long arm of chromosome 1 (1.q22-1.q23) and was cloned in 1993. It is a single copy gene and encodes a 336 amino acid acidic glycoprotein. The gene carries the antigenic determinants of the Duffy blood group system consisting of four alleles—FY*A and FY*B—coding for the Fya and Fyb antigens respectively, FY*X and FY*Fy, five phenotypes (Fy-a, Fy-b, Fy-o, Fy-x and Fy-y) and five antigens. Fya and Fyb differ by in a single amino acid at position 43: aspartic acid in Fya and glycine in Fyb. The genetic basis for the Fy(a−b−) phenotype is a point mutation in the erythroid specific promoter.

As noted above, the second antigen can comprise any antigen against which the raising of an antibody is desired. Thus, it is understood and herein contemplated that in addition to the various blood group antigens disclosed herein, the disclosed methods can also be used with antigens derived from infectious organisms (e.g., viruses, bacteria, fungi, and parasites) or other disease conditions such as a cancer. Thus, for example, it is understood that the second antigen can be a viral antigen. Viral antigens can include any peptide, polypeptide, or protein from a virus. Thus in one embodiment the second antigen can be an antigen from a virus selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed are methods wherein the second antigen is a bacterial antigen. The antigen, for example, can be a peptide, polypeptide, or protein selected from the group of bacteria consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species.

Also disclosed are methods wherein the second antigen is a fungal antigen. The antigen can be, for example, a peptide, polypeptide, or protein selected from the group of fungi consisting of *Candida albicans, Cryptococcus neoformans, Histoplama capsulatum, Aspergillus fumigatus, Coccidiodes immitis, Paracoccidiodes brasiliensis, Blastomyces dermitidis, Pneomocystis carnii, Penicillium marneffi*, and *Alternaria alternata.*

Also disclosed are methods wherein the second antigen is a parasite antigen. The antigen can be, for example, a peptide, polypeptide, or protein selected from the group of parasitic organisms consisting of *Toxoplasma gondii, Plasmodium falciparum, Plasmodium vivax, Plasmodium malariae*, other *Plasmodium* species, *Trypanosoma brucei, Trypanosoma cruzi, Leishmania major*, other *Leishmania* species, *Schistosoma mansoni*, other *Schistosoma* species, and *Entamoeba histolytica.*

Also disclosed are methods wherein the second antigen is a cancer-related antigen. The antigen can be, for example, a peptide, polypeptide, or protein selected from the group of cancers consisting of lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

It is understood and herein contemplated that the subject in the disclosed methods can be a mouse, rat, dog, cat, guinea pig, rabbit, horse, pig, cow, monkey, or chimpanzee or other non-human primate. It is also understood that the subject can be a human.

Where the subject is non-human, but the antigen is human, it is understood that transgenic animals can be used to express the human antigen. Thus, disclosed herein are methods of making a monoclonal antibody wherein the second and third antigen are human antigens. Further disclosed are methods of making a monoclonal antibody wherein the third antigen is expressed in a subject transgenic for the third antigen. Also disclosed are methods wherein the subject has been tolerized to the third antigen.

In the example given (see FIG. 1) donor and recipient express the same molecule, but with an allelic amino acid variant, depicted by Q or R. The molecule (on a cell) undergoes receptor mediated endocytosis by B cells that encode a surface immunoglobulin (i.e. the B cell receptor) specific for the antigen formed by Q. In addition, the blood group molecule is phagocytosed by professional antigen presenting cells (APCs). In both cases, the molecule is processed into peptides, which is presented on MHC class II molecules on both B cells and APCs. Presentation of peptide containing Q, by MHC class II, constitutes a foreign T cell epitope allowing CD4+ T cells to be activated by APC, thereby providing help for B cells displaying the same T cell epitope. Since Q is the only molecular difference between the donor and recipient molecules in this scenario, the MHC locus of the recipient must encode an MHC class II molecule that is able to present a peptide containing Q for a CD4+ T cell dependant immune response to occur. This very issue is in of itself critical, for it is a chance occurrence whether or not a given MHC haplotype encodes an MHC variant that can present a given peptide. In some cases this occurs only in a few strains, which must be empirically discovered. In other cases, amino acid constraints may preclude the peptide being presented by any MHC. If no MHC presents the peptide, an IgG antibody response will not occur. Because the recipient MHC (or any MHC) may not be able to present peptide containing the variant amino acid, the mice may not be able to mount an antibody response against the immunogen. This severely limits the immunogenicity of the antigen.

In the approach described herein, a synthetic MHC class II restricted peptide that is known to serve as a strong CD4+ T cell epitope is fused, in frame, to the terminal end of the antigen in question. This provides a peptide that can be readily processed and presented onto the recipient MHC, and serve as an epitope for CD4+ T cells.

Although the above fusion protein has a strong T cell epitope, this alone is insufficient to give a strong antibody response. The reason is that the precursor frequency of CD4+ T cells that recognize any given epitope in a naïve animal is very low. Moreover, as above, in the realm of antigenic stimuli, antigens on cells can be a very weak stimulus; in some cases they can even lead to an undesired effect of tolerance. To circumvent these obstacles, the peptide that constitutes the fused T cell epitope is administered to a subject, in order to prime the subject in the CD4+ T cell compartment. However, this can also result in a strong antibody response against the peptide itself, which can compete with the desired epitope. Rather, the approach described herein evolves by specifically selecting a fusion CD4+ T cell epitope peptide for which there already exists a TCR transgenic mice, which express a T cell receptor (TCR) specific for the peptide presented by a given murine MHC. In such TCR transgenic mice, the vast majority of CD4+ T cells are specific for the chosen CD4+ T cell epitope. Accordingly, the precursor frequency of CD4+ T cells specific for the fused peptide can be substantially increased by adoptive transfer of CD4+ T cells from the TCR transgenic animal into a wild-type animal, prior to immunization with the cells expressing the fusion protein antigen. Then, when the antigen is introduced by injecting cells, CD4+ T cell help is enhanced by orders of magnitude resulting in a very strong antibody response. As the B cell repertoire is restricted due to B cell tolerance against the other components of the antigen, due to tolerance against the transgene in the recipient, a strong focused response occurs against the desired epitope. Finally, such high levels of help facilitate class switching and affinity maturation, allowing the generation of high affinity monoclonal antibody reagents.

Alternative methods consist of making a transgenic mouse that expresses one allelic form of the protein in question. This animal is then immunized with the second allelic form. Since the animal is tolerized to the allelic form that it expresses as a transgene, its antibody response is immunologically focused on the differences found in the second allelic form. However, without help, the response may still be weak and also requires that purified protein be used, which as above is not viable for epitopes that require the natural transmembrane conformation. The current invention utilizes this above approach, but improves the system by allowing a novel cellular adjuvant to substantially focus the immune response to the epitope in question and dramatically increase the immunogenicity of cells expressing the antigen. Moreover, the protein is not presented as a purified protein but in its natural confirmation being expressed on the surface of a cell.

As disclosed herein, the disclosed methods can be used for detection of allelic variations beyond blood group antigens. For example, the disclosed methods can be used to detect allelic variants between hemoglobin, albumin, or cardiac enzymes humans. Such methods would be useful in typing and monitoring transplanted tissue and transplant recipients.

Additionally, the disclosed methods can be used to generate antibodies against minor epitopes or epitopes that are not typically present in an acute situation but become prevalent in a chronic infection or where there is an escape mutant. For example, the disclosed methods can be used to generate neutralizing antibodies against Human Immunodeficiency Virus (HIV). In HIV, neutralizing antibodies are typically not generated because the immunodominant humoral epitopes are not neutralizing targets; however, such epitopes so completely dominate the humoral response that the more effective neutralizing antibodies are never formed. Similarly, in a viral infection such as Lymphocytic Choriomeningitis Virus (LCMV), the T cell response so rapidly controls the infection, the antibody responses are often relatively weak or not even generated. However, in a chronic infection, LCMV specific T cells targeted to immunodominant epitopes become exhausted and lose functionality. Thus the virus escapes elimination and can progress if not controlled by immune responses to previously subdominant epitopes which have become dominant by virtue of the loss of the immunodominant epitope. The present methods allow for the generation of antibodies against the otherwise weak epitopes or humoral epitopes masked by the immunodominant response. By utilizing the methods disclosed herein, better vaccine targets can be discovered and exploited. Antibodies generated using the disclosed methods can be used alone as a vaccine or as a component to a vaccine. Additionally, the epitopes detected using this technology can be utilized as a component to a more thorough vaccine. For example, a immunosubdominant epitope that becomes dominant in chronic infections can be used as a component to a peptide vaccine which otherwise would focus on the acute immunodominant epitopes. When the vaccine is administered to a subject, immune response is generated to the immunodominant epitopes as well as the now amplified subdominant epitope allowing for much better control against infection. Similarly, for infectious agents, such as, for example, HIV, the discovery and generation of antibodies against neutralizing epitopes allows for more effective humoral control of the virus. Thus, the disclosed methods can be used to amplify otherwise weak or subdominant epitopes as well as to generate antibodies against said epitopes. Through the identification of these epitopes new targets against an infectious agent can be generated. Also, the epitopes and any antibodies against said epitopes can be used alone or in combination in prophylactic or therapeutics vaccines.

Additionally, by chemically linking a hapten to the antigen carrying the T cell epitope recognized by a TCR transgenic animal (or CD4 T cell line), antibody responses against small hapten chemical moieties can be amplified.

It is further disclosed that the methods disclosed herein can be used to generate monoclonal antibodies to a protein in the same animal species from which that protein was derived. By fusing a CD4 epitope to an antigen to which the animal is tolerant, autoantibodies can be induced. For example, generating monoclonal antibodies to a mouse protein in a mouse. It is understood that such method is applicable to any animal including but not limited to mouse, rat, hamster, guinea pig, rabbit, cat, dog, sheep, cow, horse, monkeys, chimpanzees, and other non-human primates.

C. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular monoclonal antibody is disclosed and discussed and a number of modifications that can be made to a number of molecules including the monoclonal antibody are discussed, specifically contemplated is each and every combination and permutation of the monoclonal antibody and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed herein are monoclonal antibodies specific for single amino acid variation in an antigen. It is understood and herein contemplated that the disclosed monoclonal antibodies can be specific for any antigen. The disclosed monoclonal antibodies are useful in any situation where specificity capable of detecting single amino acid variation is important. For example, the disclosed antibodies are useful for distinguishing between variants of a blood antigen such as the Duffy antigen. Thus, in one aspect the disclosed monoclonal antigens are specific for blood antigens. For example, the disclosed monoclonal antibodies can be specific for a blood antigen wherein the blood antigen is selected from the list of blood antigens consisting of ABO, MNS, P, Rh, Lutheran ($Lu^a$ and $Lu^b$), Kell and XK, Lewis ($Le^a$ and $Le^b$), Duffy ($Fy^a$ and $Fy^b$), Kidd ($Jk^a$ and $Jk^b$), Diego, XG, Scianna, Dombrock, Colton, Landsteiner-Wiener, Cartwright (Yt), Chido-Rogers, H substance (Hh), Kell precursor (Kx), Gerbich, Cromer, Knops, Indian, OK, Xg, Raph, John Milton Hagen (JMH), GIL, Cost, Er, Batty, Christiansen, Biles, Box, Torkildsen, Peters, Reid, Jensen, Livesey, Milne, Rasmussen, Oldeide, JFV, Katagiri, Jones, HJK, HOFM, SARAH, REIT, VEL, Lan Ata, Jra, Emm, AnWj, Sda PEL, ABTI, and MAM. In particular, disclosed herein are monoclonal antibodies specific for a blood antigen wherein the blood antigen is selected from the list of blood antigens consisting of Duffy A, Duffy B, Kell antigen $K_1$, Kell antigen $K_2$, S antigen, H substance, Yt(a), and Yt(b). It is further understood and herein contemplated that any antibody described herein can be a human antibody.

Further disclosed are antibodies made using the methods disclosed herein. It is understood and herein contemplated that the antibodies disclosed herein are useful beyond mere detection of allelic variants which can be used in tissue typing. The disclosed antibodies also have uses in studying antibody responses to antigens where an immunodominant T cell response masks any humoral response or removes the antigen completely before a humoral response can be generated. XXX. The disclosed antibodies can also be used in functional roles as agonistic or antagonistic antibodies.

1. Antibodies 1

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody" and "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain $Fy^a$, $Fy^b$, or other blood antigen binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. *Antibodies, A Laboratory Manual*. Cold Spring Harbor Publications, New York, (1988)). Also included within the meaning of "antibody" are conjugates of antibody fragments and antigen binding proteins (single chain antibodies) sFv, scFv, as described, for example, in U.S. Pat. No. 4,704,692, the contents of which are hereby incorporated by reference.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975) or Harlow and Lane. *Antibodies, A Laboratory Manual*. Cold Spring Harbor Publications, New York, (1988). In a hybridoma method, a mouse or other appropriate host animal is typically immunized with an immunizing agent to elicit lymphocytes that produce or are capable of producing antibodies that specifically bind to the immunizing agent. Alternatively, the lymphocytes may be immunized in vitro, e.g., using the HIV Env-CD4-co-receptor complexes described herein.

In one aspect, the immunizing agent comprises an allelic variant of an endogenous antigen. Traditionally, the generation of monoclonal antibodies has depended on the availability of purified protein or peptides for use as the immunogen. More recently DNA based immunizations have shown promise as a way to elicit strong immune responses and generate monoclonal antibodies.

An alternate approach to immunizations with either purified protein or DNA is to use antigen expressed in baculovirus. The advantages to this system include ease of generation, high levels of expression, and post-translational modifications that are highly similar to those seen in mammalian systems. This system results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.,* 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against blood antigens including but not limited to, for example, ABO, MNS, P, Rh, Lutheran ($Lu^a$ and $Lu^b$), Kell and XK, Lewis ($Le^a$ and $Le^b$), Duffy ($Fy^a$ and $Fy^b$), Kidd ($Jk^a$ and $Jk^b$), Diego, XG, Scianna, Dombrock, Colton, Landsteiner-Wiener, Cartwright (Yt), Chido-Rogers, H substance (Hh), Kell precursor (Kx), Gerbich, Cromer, Knops, Indian, OK, Xg, Raph, John Milton Hagen (JMH), GIL, Cost, Er, Batty, Christiansen, Biles, Box, Torkildsen, Peters, Reid, Jensen, Livesey, Milne, Rasmussen, Oldeide, JFV, Katagiri, Jones, HJK, HOFM, SARAH, REIT, VEL, Lan Ata, Jra, Emm, AnWj, Sda PEL, ABTI, MAM, or any other antigen disclosed herein. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., *Proc. Natl. Acad. Sci. USA,* 90:2551 (1993); Jakobovits et al., *Nature,* 362:255-258 (1993); Bruggemann et al., *Year in Immuno.,* 7:33 (1993)). Human antibodies can also be produced in phage display libraries (Hoogenboom et al., *J. Mol. Biol.,* 227:381 (1991); Marks et al., *J. Mol. Biol.,* 222:581 (1991)). The techniques of Cote et al. and Boerner et al. are also available for the preparation of human monoclonal antibodies (Cole et al., *Monoclonal Antibodies and Cancer Therapy*, Alan R. Liss, p. 77 (1985); Boerner et al., *J. Immunol.,* 147(1):86-95 (1991)). It is understood that the F-PEAT methods described herein can be used in conjunction with phage display production of antibodies.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, *Antibodies, A Laboratory Manual*, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry,* 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. *Science,* 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) *FEBS Lett.* 307:97-101; Clark-Lewis I et al., *J. Biol. Chem.,* 269:16075 (1994); Clark-Lewis I et al., *Biochemistry,* 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science,* 256:221 (1992)). This technique has been used to synthesize analogs of protein domains as well as large amounts of relatively pure proteins with full biological activity (deLisle Milton R C et al., *Techniques in Protein Chemistry IV.* Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with Duffy antigens $Fy^a$ or $Fy^b$. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. *Nucl. Acids Res.* 10:6487-500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. *Antibodies, A Laboratory Manual.* Cold Spring Harbor Publications, New York, (1988), for a description of immunoassay formats and conditions that can be used to determine selective binding. The binding affinity of a monoclonal antibody can, for example, be determined by the Scatchard analysis of Munson et al., *Anal. Biochem.,* 107:220 (1980).

Also provided is an antibody reagent kit comprising containers of the monoclonal antibody or fragment thereof and one or more reagents for detecting binding of the antibody or fragment thereof to a blood antigen. The reagents can include, for example, fluorescent tags, enzymatic tags, or other tags. The reagents can also include secondary or tertiary antibodies or reagents for enzymatic reactions, wherein the enzymatic reactions produce a product that can be visualized.

As used herein, the term “antibody” or “antibodies” can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(1) Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.,* 147(1):86-95, 1991). Human antibodies (and fragments thereof) can also be produced using phage display libraries (Hoogenboom et al., *J. Mol. Biol.,* 227:381, 1991; Marks et al., *J. Mol. Biol.,* 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germline mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(2) Humanized Antibodies

Optionally, the antibodies are generated in other species and “humanized” for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature,* 321:522-525 (1986); Riechmann et al., *Nature,* 332:323-327 (1988); and Presta, *Curr. Op. Struct. Biol.,* 2:593-596 (1992)).

Methods for humanizing non-human antibodies are well known in the art. Generally, a humanized antibody has one or more amino acid residues introduced into it from a source that is non-human. These non-human amino acid residues are often referred to as “import” residues, which are typically taken from an “import” variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such “humanized” antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377.

The choice of human variable domains, both light and heavy, to be used in making the humanized antibodies is very important in order to reduce antigenicity. According to the “best-fit” method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.,* 151:2296 (1993) and Chothia et al., *J. Mol. Biol.,* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

2. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, ligand type, ligand valency, and ligand concentration. Molecular and cellular mechanisms of receptor-mediated endocytosis has been reviewed (Brown and Greene, *DNA and Cell Biology* 10: 399-409 (1991)).

Disclosed herein is a vector comprising a gene for a B-cell antigen fused to a MHC class II restricted antigen. Also disclosed herein is a vector comprising a gene for a B-cell antigen, wherein the B cell antigen is comprises one of several allelic variants of an antigen or an antigen for which the antigen of interest differs by a single amino acid variation. Thus, for example, disclosed herein are vectors encoding a human blood cell antigen. Also disclosed herein are cells comprising the disclosed vectors. It is further understood and herein contemplated that the disclosed vectors and cells can be administered to an animal. It is further understood, that such animal can be transgenic such as a transgenic mouse. Therefore, disclosed herein are transgenic animals comprising the disclosed cells and vectors. Thus, for example, are transgenic animals comprising a cell comprising a vector encoding a human blood cell antigen.

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms/disorder are/is effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

Following administration of a disclosed composition, such as an antibody, for treating, inhibiting, or preventing a blood incompatibility reaction such as hemolytic disease of the newborn (including but not limited to ABO hemolytic disease, Rhesus D hemolytic disease, Rhesus C hemolytic disease, anti-Kell hemolytic disease, and anti-Duffy hemolytic disease) or Alloimmune hemolytic disease, the efficacy of the therapeutic antibody can be assessed in various ways well known to the skilled practitioner. For instance, one of ordinary skill in the art will understand that a composition, such as an antibody, disclosed herein is efficacious in treating or inhibiting an a blood incompatibility reaction in a subject by observing that the composition reduces antibodies specific to the incompatible blood antigen or prevents a further increase in blood antigen specific antibodies.

"Treatment" means a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. For example, a disclosed method for reducing the effects of a hemolytic disease is considered to be a treatment if there is a 10% reduction in one or more symptoms of the disease (e.g., tumor size) in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is also understood and contemplated herein that treatment can refer to any reduction in the progression of a disease. Thus, for example, methods of reducing the effects of a hemolytic disease is considered to be a treatment if there is a 10% reduction in the tumor growth rate relative to a control subject or tumor growth rates in the same subject prior to the treatment. It is understood that the reduction can be a 10, 20, 30, 40, 50, 60, 70, 80, 90, 100%, or any amount of reduction in between as compared to native or control levels. It is understood and herein contemplated that treatment can refer to prophylactic treatment or therapeutic treatment. Thus, for example, treating a mother against hemolytic disease of the newborn would be the administration of anti-blood antigen antibodies to the mother before endogenous antibodies can be formed at all or at least in large quantities in the treated mother.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels. Thus, for example, inhibition can refer to any reduction or ablation of anti-blood antigen antibodies in a mother relative to a control.

It is understood and herein contemplated that inhibit can refer to prophylactic inhibition or therapeutic inhibition.

Other molecules that interact with the blood antigens disclosed herein which do not have a specific pharmaceutical function, but which may be used for tracking changes within cellular chromosomes or for the delivery of diagnostic tools for example can be delivered in ways similar to those described for the pharmaceutical products.

The disclosed compositions and methods can also be used for example as tools to isolate and test new drug candidates for a variety of blood antigen related diseases.

D. METHODS OF USING THE COMPOSITIONS

The antibodies disclosed herein or made using the disclosed methods have many uses such as in the typing of tissue, screening of donors, assessing the risk of hemolytic disease of the newborn. Thus, disclosed herein are methods of typing a tissue sample or screening for blood incompatibility comprising a) obtaining a tissue sample from a subject; b) contacting the antibodies disclosed herein with the tissue; and c) determining for the presence of binding of the antibody to the tissue. It is further understood that the disclosed antibodies have use in any method or assay in which antibodies are employed.

The disclosed methods are particularly useful for typing tissue in situations where the subject has antigen-specific humoral autoimmunity such as autoimmune hemolytic anemia. Such automimmune conditions can also include but are not limited to asthma, rheumatoid arthritis, reactive arthritis, spondylarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, ischemia reperfusion injury, myocardial infarction, Alzheimer's disease, transplant rejection (allogeneic and xenogeneic), thermal trauma, any immune complex-induced inflammation, glomerulonephritis, myasthenia gravis, cerebral lupus, Guillaine-Barre syndrome, vasculitis, systemic sclerosis, anaphylaxis, catheter reactions, atheroma, infertility, thyroiditis, ARDS, post-bypass syndrome, hemodialysis, juvenile rheumatoid, Behcets syndrome, hemolytic anemia, pemphigus, bulbous pemphigoid, stroke, atherosclerosis, and scleroderma. Phenotyping of patient's RBCs is problematic in the context of a patient who needs a transfusion due to autoimmune hemolytic anemia. The reason for this is that many of the typing antibodies are human and require a secondary antibody to induce agglutination. Since the patient's own RBCs are already coated with antibody (i.e. the autoantibody), the secondary antibody spontaneously agglutinates all cells. This creates a background situation in which all samples give a false positive. However, the disclosed antibodies and methods can be used to generate a panel of all murine antibodies. By using murine antibodies, a mouse specific secondary reagent that doesn't' interact with human IgG can be used. In this way, the background would be eliminated, thus allowing phenotyping in this patient population. Therefore, disclosed herein are methods of typing a tissue sample or screening for blood incompatibility wherein the subject has antigen-specific humoral autoimmunity such as autoimmune hemolytic anemia.

The antibodies disclosed herein are also useful in determining the risk of blood diseases that exist following primary exposure to incompatible blood antigens. Examples of such a disease is hemolytic disease of the newborn (including but not limited to ABO hemolytic disease, Rhesus D hemolytic disease, Rhesus C hemolytic disease, anti-Kell hemolytic disease, and anti-Duffy hemolytic disease), Alloimmune hemolytic disease, Systemic lupus erythematosus, and Evans' syndrome. In hemolytic disease of the newborn, there is blood incompatibility between a mother and child such as an Rh− (negative) mother giving birth to a Rh+ (positive) child. There, a first child born to a mother with incompatible blood antigens does not suffer any risk as the mother would not have been exposed to the incompatible blood antigen and would not have antibodies to the incompatible antigen. However, a second child with incompatible blood would pose great risk to mother and child. One method to determine if there is a risk for hemolytic disease of the newborn involves typing the blood of both parents where incompatible blood between the mother and father indicates risk of hemolytic disease of the newborn. Thus disclosed herein are methods of assessing the risk for hemolytic disease of the newborn comprising a) determining if a pregnancy is the first or subsequent pregnancy for the mother; b) obtaining a tissue sample from the mother and father; c) separately contacting the antibodies disclosed herein with the tissue; and d) determining the presence of binding of the antibody to the tissue and comparing the presence of binding between the parent, wherein a different result indicates the risk of hemolytic disease of the newborn. It is understood and herein contemplated that in many cases risk of hemolytic disease of the newborn only exists where the mother would have antibodies against the father's blood antigens such as when a mother is Rh− (negative) and the father is Rh+ (positive), but would not exist where the mother is Rh+ (positive) and the father is Rh− (negative). One of skill in the art would be able to make such assessment.

When there is risk of hemolytic disease of the newborn, a known method of preventing hemolytic disease of the newborn in the subsequent children is through the administration of antibodies to the mother following delivery of the first incompatible child. For example, where there is an Rh− (negative) mother and a first Rh+ (positive) child, following delivery, anti-Rh antibody is administered to the mother to reduce the chance that the mother will generate her own anti-Rh antibodies. Therefore, disclosed herein are methods of preventing hemolytic disease of the newborn comprising administering to a mother an antibody disclosed herein or generated by the methods disclosed herein following delivery of a child with an incompatible blood antigen.

It is understood that the subject in the disclosed methods can be a mouse, rat, dog, cat, hamster, guinea pig, rabbit, horse, pig, cow, monkey, chimpanzee, or other non-human primate. It is also understood that the subject can be a human.

It is understood that the disclosed methods can be used with any tissue. Thus, for example, the tissue can be blood, bone marrow, or tissue from an organ such as liver, heart, muscle, lung, kidney, or spleen.

There are many assays known in the art that can be used to detect binding of the disclosed antibodies to an antigen. Thus disclosed herein are methods, wherein the presence of binding is determined by conducting an immunoassay. Thus, for example, disclosed are methods wherein the immunoassay is selected from the group consisting of agglutination (including but not limited to DAT and IAT), ELISA, ELIspot, Flow cytometry, Immunofluorosence assay; and Immunohistochemical assay.

The disclosed compositions can be used as discussed herein as either reagents in micro arrays or as reagents to probe or analyze existing microarrays. It is further understood that the disclosed compositions can be used in any known method for isolating or identifying single nucleotide polymorphisms. The compositions can also be used in any method for determining allelic analysis of a blood antigen, for example, Duffy antigen. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

1. Immunoassays

The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), enzyme linked immunospot assay (ELIspot), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), hemagglutination assay, immunoprecipitation, immunofixation, immunodiffusion, immunoelectrophoresis, immunodepletion, latex agglutination assay, Coombs' test, Coombs' test variants using anti-mouse, anti-rabbit, anti-rat, or anti-guinea pig reagents, and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, ELISpot plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Examples of fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll;

Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); 1Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); fluorescein isothiocyanate (FITC); Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium lodid (Pl); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in this aspect include, but are not limited to, Tc-99m, Re-186, Ga-68, Re-188, Y-90, Sm-153, Bi-212, Cu-67, Cu-64, and Cu-62. Radiolabeling techniques such as these are routine in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

It is understood that direct or indirect detection can also occur with agglutination assays such as hemagglutination assay, latex agglutination assay, Coombs' test (including both direct agglutination test (DAT) and indirect agglutination test (IAT), and Coombs' test variants using anti-mouse, anti-rabbit, anti-rat, or anti-guinea pig reagents. In direct Coombs' test, for example, direct detection is accomplished by adding Coomb's reagent directly to a sample of the subject blood. If the subject has autoimmune hemolytic anemia, the blood will agglutinate. In indirect Coombs' test, for example, indirect detection is accomplished by contacting antibody to an antigen (usually present on the surface of a red blood cell (RBC) of predetermined antigenicity) and then detecting the presence of antibody bound to antigen by the addition of Coombs' reagent (anti-human globulin). It is understood that the disclosed methods contemplate the use of reagents that overcome difficulties with the anti-human Coombs' test associated with autoimmune hemolytic anemia where the patients own antibodies will agglutinate upon contact with the Coombs'reagent resulting in a false positive. Thus, contemplated herein are Coombs' reagents comprising anti-mouse globulin, anti-rat-globulin, anti-rabbit globulin, or anti-guinea pig globulin.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody—antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250: 4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121: 321349 (1964), each of which is herein incorporated by reference in its entirety for teachings regarding electrophoresis methods.

Laemmli, U. K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., *Protein Methods* (2d edition 1996) and E. Harlow & D. Lane, *Antibodies, a Laboratory Manual* (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper or membranes, can be used. The proteins retain the same pattern of separation as on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis—I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at <http://www.promega.com/faq/gelshfaq.html> (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}I$ or $^{131}I$ are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites and at higher concentrations of cold antigen, more binds to the antibody, displacing the radioactive variant. The bound antigens are separated from the unbound ones in solution and the radioactivity of each used to plot a binding curve.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995; U.S. Pat. No. 4,376,110, each of which is incorporated herein by reference in its entirety and specifically for teachings regarding ELISA methods.

Variations of ELISA techniques are know to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

"Under conditions effective to allow immunecomplex (antigen/antibody) formation" means that the conditions include diluting the antigens and antibodies with solutions such as BSA, bovine gamma globulin (BGG) and PBS/Tween so as to reduce non-specific binding and promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibody cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialized chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include colour coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilised on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; Bioinvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UVactivated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labeling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

2. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits can include antibodies discussed in certain embodiments of the methods, as well as the buffers and enzymes required to use the primers as intended. For example, disclosed is a kit for assessing the risk of hemolytic disease of the newborn comprising a monoclonal antibody sufficient in quantity to test two individuals and a detection method. Also disclosed herein are kits for typing a tissue sample from a subject comprising a monoclonal antibody directed against a blood antigen; a secondary antibody; and a detection method.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated, parts are parts by weight, temperature is in ° C. or is ambient temperature, and pressure is at or near atmospheric.

1. Example 1

Monoclonal Antibodies for Blood Group Antigens

Although monoclonal antibody reagents exist and are commercially available for the majority of blood group antigens, there remain a number of blood group antigens for which no monoclonal antibodies have been described. These include both common antigens (i.e. $Fy^a$, $Fy^b$ and s, and numerous different rare subtypes of RhD.), and rare antigens. One can make monoclonal antibodies from transformation of human circulating B cells derived from alloimmunized patients, but the human approach can be technically difficult, often with disappointing results. Additional approaches that do not require immunization of an animal include phage display technology, which is a promising approach. However, immunization of mice is a well established method of generating monoclonal antibodies for RBC typing. Moreover, murine monoclonal antibodies have several distinct advantages over human monoclonal antibodies when applied to analysis of patient RBCs.

Despite the general utility of mice for making monoclonal antibody reagents, and the advantages of murine monoclonal antibodies, technical obstacles exist when making antibodies against certain human RBC antigens. This application describes a novel approach to circumventing existing barriers in the development of murine monoclonal antibodies against human blood group antigens using the Fusion-Peptide Epitope Adoptive Transfer (F-PEAT) technology. The significance of the F-PEAT technology is that it allows the generation of a panel of clinically useful murine antibodies, against human blood group antigens, which cannot be made by existing technologies.

Monoclonal antibody reagents have distinct advantages over patient antisera, including: 1) essentially an unlimited supply of reagent, 2) consistency over time, and 3) absence of issues surrounding donor recruitment. However, there is an additional and substantial advantage to using an antibody reagent that is derived from a non-human species. It is not uncommon for transfusion recipient patients to develop autoantibodies that agglutinate their own RBCs, which can lead to autoimmune hemolytic anemia, but are often clinically benign. Moreover, approximately 1/100 healthy blood donors have clinically benign autoantibodies, which are only detected upon blood donation. In the routine practice of blood banking immunohematology, it is often necessary to phenotype the antigens expressed by both donor and recipient RBCs. However, autoantibodies substantially interfere in this process, as all RBCs agglutinate. This obfuscates the detection of blood group antigens by agglutination, as all specimens spontaneously agglutinate, bringing the background noise of the assay to essentially 100%. However, many of these autoantibodies only exhibit their activity at the Coombs phase (i.e. they only agglutinate in the presence of anti-human globulin). Murine monoclonal antibodies can be induced to agglutinate with anti-mouse globulin, which does not cross-react with human antibodies and thus does not agglutinate RBCs coated with human autoantibodies. In addition, even for autoantibodies that agglutinate on their own (in the absence of anti-human globulin), murine monoclonal antibodies can easily be conjugated to fluorochromes, allowing phenotyping by flow cytometry which uses a non-agglutination based approach to phenotyping RBCs. Thus, in addition to the above advantages, murine monoclonals can be used to phenotype RBC antigens despite the presence of autoantibodies that prevent phenotyping of RBCs in certain donors and patients. Hence even for antigens for which human monoclonal typing reagents exist, the generation of additional murine monoclonals has distinct advantages.

Generation of murine monoclonal antibodies has now been standardized to the point that it is essentially a routine procedure, carried out by multiple facilities, both at academic centers and through corporations that specialize in custom antibody production for their customer base. However, unlike monoclonal antibody generation to most antigens, isolation of antibodies that can be utilize in characterizing expression of antigens on human RBCs presents several unique technical challenges, which are presented below.

a) Focusing the Epitope Response:

With only a few exceptions, blood group antigens consist of small polymorphisms (typically single amino acid changes), between donor and recipient. For example, the difference between Duffy A ($Fy^a$) and Duffy B ($Fy^b$) consists of a glycine to aspartic acid change at position 42 (Gly42Asp). Thus, patients who are Fy(a+b−) can make an anti $Fy^b$ if exposed to $Fy^b$+RBCs. Inversely, patients who are Fy(a−b+) can make anti-$Fy^a$ if exposed to $Fy^a$+RBCs. Except in very rare examples, patients do not make antibodies against other parts of the Duffy molecule, as it is present in both donor and recipient and is seen as immunological self; antibody responses are prevented by both central and peripheral tolerance mechanisms. Although Fy(a−b−) patients exist, the vast majority still express the Duffy protein as a self-antigen, but carry a promoter mutation that prevents expression on RBCs.

For an anti-$Fy^a$ or anti-$Fy^b$ blood typing reagent to be specific, it must bind an epitope with a requirement for the correct amino acid at position 42. Although mice have homologues to many human blood group antigens, the level of identity at the amino acid level is quite low. Thus, when a mouse is immunized with a human blood group antigen (i.e. $Fy^a$ or $Fy^b$), numerous antibodies are made against a variety of epitopes found throughout the Duffy molecule. The immunodominant response is focused on several parts of the molecule in common to all RBCs that express Duffy, regardless of whether they carry the $Fy^a$ or $Fy^b$ polymorphism. Such reagents are not capable of typing patients for $Fy^a$ or $Fy^b$. This defines the problem of focusing murine immune responses to the polymorphisms responsible for human blood group antigens. Whereas humans have a very narrow immune response focused only on allelic polymorphisms (due to immune tolerance against all non-polymorphic regions of the molecule), the murine response is against all parts of the molecule and fails to generate antibodies that can determine human polymorphisms.

This problem can be solved by recapitulating the scenario in human immunization (described above) by making a mouse transgenic for one allele of an antithetical antigen (in this case $Fy^b$), and then immunizing it with the other antithetical antigen ($Fy^a$). In this way, like a human transfusion recipient, the recipient mouse is tolerant to all the epitopes on the human molecule except the epitope created by the antithetical mutation, as this is not self. This focuses the immune response to the antithetical epitope, thus allowing the generation of the desired antibody.

b) Conformation Dependant Epitopes:

A number of blood group molecules are multi-pass transmembrane proteins, and the blood group antigens can be dependant upon the conformation of the protein. In the case of such antigens, synthetic peptides, or even purified recombinant proteins are incapable of eliciting an antibody that recognizes the desired epitope, as the synthetic immunogens fail to recapitulate the natural topology of a transmembrane protein inserted into a cellular surface. In these cases, it is necessary to use whole cells expressing the protein as an immunogen. However, using whole cells as immunogens can also present a problem, in that multiple additional foreign antigens typically exist on the cell line surface. Thus, only a small percentage of the antibody response is against the transfected protein. Thus, one must screen a substantially greater number of hybridomas to isolate antibodies specific for the desired antigen, and this can make it difficult to obtain the desired antibody.

c) Presentation of CD4+ T Cell Epitopes by Recipient MHC II.

The focusing of the immune response to the desired epitope, via making the immunization recipient transgenic for the antithetical antigen is necessary to allow the isolation of the correct antibody. However, it also has the effect of significantly decreasing the overall immunogenicity of the antigen, since the overall difference between the antigen and the recipient is now only a single amino acid. This manifests itself most profoundly at the level of the CD4+ T cell help. Unlike B cells that recognize intact antigen, $CD4^+$ T cells respond to peptide presented by MHC II. Accordingly, for any given antigen to be immunogenic, the MHC II from the recipient must be able to present an antigen derived peptide containing a foreign amino acid sequence. MHC is amongst the most highly variable genes in the mammalian genome, and each MHC presents different peptides. In this case, there is only a single amino acid difference between donor and recipient. Thus, the recipient MHC II must be able to present a peptide containing the amino acid difference that constitutes the blood group antigen. Thus, for a given mouse strain, the MHC may not be able to present a peptide containing the variant amino acid. Moreover, some peptides are not presented by MHC II molecules in general, due to prohibitive steric hindrance from certain amino acid residues. Overall, this has the potential to make some blood group antigens very weak immunogens due to the limited number of CD4+ T cell epitopes and the possibility that some strains (or occasionally all strains) will be unable to present the variant peptide as a CD4+ T cell epitope.

In the example given (see FIG. 1) Donor and recipient express the same molecule, but with an allelic amino acid variant, depicted by Q or R. The molecule (on a cell) undergoes receptor mediated endocytosis by B cells that encode a surface immunoglobulin (i.e. the B cell receptor) specific for the antigen formed by Q. In addition, the blood group molecule is phagocytosed by professional antigen presenting cells (APCs). In both cases, the molecule is processed into peptides, which is presented on MHC class II molecules on both B cells and APCs. Presentation of peptide containing Q, by MHC class II, constitutes a foreign T cell epitope allowing CD4+ T cells to be activated by APC, thereby providing help for B cells displaying the same T cell epitope. Since Q is the only molecular difference between the donor and recipient molecules in this scenario, the MHC locus of the recipient must encode an MHC class II molecule that is able to present a peptide containing Q for a CD4+ T cell dependant immune response to occur. This very issue is in of itself critical, for it is a chance occurrence whether or not a given MHC haplotype encodes an MHC variant that can present a given peptide. In some cases this occurs only in a few strains, which must be empirically discovered. In other cases, amino acid constraints may preclude the peptide being presented by any MHC. If no MHC presents the peptide, an IgG antibody response will not occur. Because the recipient MHC (or any MHC) may not be able to present peptide containing the variant amino acid, the mice may not be able to mount an antibody response against the immunogen. This severely limits the immunogenicity of the antigen.

In this approach, a synthetic MHC class II restricted peptide that is known to serve as a strong CD4+ T cell epitope is fused, in frame, to the terminal end of the antigen in question. This ensures the presence of a peptide that can be readily processed and presented by the recipient MHC II, and serve as an epitope for CD4+ T cells.

Although the above fusion protein has a strong T cell epitope, this alone is can be insufficient to give a strong antibody response. The reason is that the precursor frequency of CD4+ T cells that recognize any given epitope in a naïve animal is very low (especially in the current setting of minimal differences between donor and recipient). To circumvent this obstacle, the peptide that constitutes the fused T cell epitope is administered to the subject, in order to prime the animal in the CD4+ T cell compartment. However, this can also result in a strong antibody response against the peptide itself, which can compete with the desired epitope. Rather, in this approach fused CD4+ T cell epitope were specifically selected for which there already exists a TCR transgenic mouse, which express a T cell receptor (TCR) specific for the chosen peptide presented by a given murine MHC. In such TCR transgenic mice, the vast majority of CD4+ T cells are specific for the chosen CD4+ T cell epitope. Accordingly, this substantially increases the precursor frequency of CD4+ T cells specific for the fused peptide by adoptive transfer of CD4+ T cells from the TCR transgenic animal into a wild-type animal, prior to immunization with the cells expressing the fusion protein antigen. Then, when the antigen is introduced by injecting cells, CD4+ T cell help is enhanced by orders of magnitude resulting in a very strong antibody response. As the B cell repertoire is restricted due to B cell tolerance against the other components of the antigen, due to tolerance against the transgene in the recipient, a strong focused response occurs against the desired epitope. Finally, such high levels of help facilitate class switching and affinity maturation, allowing for the generation of high affinity monoclonal antibody reagents.

2. Example 2

Adoptive Transfer with CD4+ Cells

B6×B10.BR recipient mice were untreated or were adoptively transferred with CD4+ T cells specific for MHC class II presenting a peptide epitope from hen egg lysozyme (HEL). Both groups were then transfused with red blood cells expressing HEL on their surface. Seven days post transfusion, mice were bled, and antibody response to HEL was measured by an ELISA specific for IgG anti-HEL. Adoptive transfer of CD4+ T cells induced a substantial increase in anti-HEL IgG (FIG. 3). There were 4 mice in each group (error bars represent standard deviation).

3. Example 3

Typing Patients with Warm Autoantibodies

Even for the human blood group antigens, for which there are already good typing antibodies, an additional application can be found in the use of murine monoclonal reagents. The reason for this is that many human blood group antigen antibodies were derived from patients, and thus are human immunoglobulins. This has been necessary precisely for the reasons detailed above, i.e. mouse antibodies are often lacking the fine specificity required to be useful typing reagents. The technical limitation of utilizing human antibodies is found in the subset of patients who have a warm autoantibody. In this instance, it is impossible to phenotype the patient's red blood cells using serology, as the red cells come up positive for every typing antibody, due to the fact that they are already coated with human antibody and therefore, agglutinate with Coombs reagent. However, it is quite possible to generate a Coombs reagent that is specific to murine antibodies and does not recognize human antibodies. This reagent would not agglutinate human red cells coated with autoantibody, but would agglutinate human red blood cells coated with antibodies of murine origin. In this way, by utilizing murine typing reagents and murine specific Coombs reagent, one can phenotype red blood cells from patients with warm autoantibody. Thus, generating novel murine monoclonal antibodies against antigens for which there are already human monoclonal antibodies has additional utility in typing patients who have warm autoantibodies.

What is claimed is:

1. A method of making a monoclonal antibody comprising the steps of a. administering to a subject CD4 T cells from a donor specific for a first antigen, wherein said CD4 T cells are of the same species as the subject and the donor and subject are MHC matched;

b. administering to a subject a cell comprising a chimeric antigen wherein the chimeric antigen comprises a first antigen linked to the terminal end of a second antigen, wherein the subject expresses a third antigen and wherein the third antigen differs from the second antigen by a single amino acid variation; and c. generating a monoclonal antibody specific to the second antigen.

2. The method of claim 1, wherein the subject is a mammal.

3. The method of claim 2, wherein the mammal is a mouse.

4. The method of claim 1, wherein the subject is transgenic for the third antigen.

5. The method of claim 1, wherein the subject is tolerized to the third antigen.

6. The method of claim 1, wherein the first antigen is a CD4 T cell epitope.

7. The method of claim 1, wherein the CD4 T cells are isolated from a second subject comprising T-cell receptor (TCR) transgene specific for the first antigen.

8. The method of claim 1, wherein the CD4 T cells are derived from a CD4 T cell line.

9. The method of claim 1, wherein the second antigen is a blood antigen.

10. The method of claim 9, wherein the blood antigen is selected from the listing of blood antigens consisting of Duffy A, Duffy B, Kell antigen $K_1$, Kell antigen $K_2$, S antigen, H substance, Yt(a), and Yt(b).

* * * * *

UNITED STATES PATENT AND TRADEMARK OFFICE

CERTIFICATE OF CORRECTION

PATENT NO. : 8,697,846 B2
APPLICATION NO. : 12/671926
DATED : April 15, 2014
INVENTOR(S) : James C. Zimring It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 708 days.

Signed and Sealed this
Twenty-ninth Day of September, 2015

Michelle K. Lee
*Director of the United States Patent and Trademark Office*